United States Patent [19]

Mayol

[11] 4,318,899

[45] Mar. 9, 1982

[54] ENCAINIDE ASSAY METHOD

[75] Inventor: Robert F. Mayol, Evansville, Ind.

[73] Assignee: Mead Johnson & Company, Evansville, Ind.

[21] Appl. No.: 155,338

[22] Filed: Jun. 2, 1980

Related U.S. Application Data

[63] Continuation of Ser. No. 971,180, Dec. 20, 1978, abandoned.

[51] Int. Cl.$^3$ ............... G01N 33/56; G01N 33/58; C07G 7/00; C07D 211/32
[52] U.S. Cl. .................. 424/1; 23/230 B; 260/112 R; 260/112 B; 424/12; 546/234
[58] Field of Search ............ 424/1, 12; 23/230 B; 260/112 B, 112 R; 546/234

[56] References Cited

U.S. PATENT DOCUMENTS 3,931,195  1/1976  Dykstra et al. ............... 546/234
4,070,492  1/1978  Spector ........................... 424/1

OTHER PUBLICATIONS

Mayol et al., Therapeutic Drug Monitoring, 1:507–524 (1979).
Byrne, et al., J. Pharmacol. Exp. Thera., 200:147–154 (1977).

*Primary Examiner*—Christine M. Nucker
*Attorney, Agent, or Firm*—Robert H. Uloth; Robert E. Carnahan

[57] ABSTRACT

A reliable and sensitive immunoassay for encainide in biological fluids including a novel hapten required for antigen synthesis and an immunologically homologous labeled tracer is provided.

9 Claims, No Drawings

ENCAINIDE ASSAY METHOD

REFERENCE TO RELATED APPLICATION

This application is a continuation of U.S. Ser. No. 971,180 filed Dec. 20, 1978, abandoned.

FIELD OF THE INVENTION

This invention refers to a test method for quantitative measurement of encainide in fluids including biological fluids which employs an antiserum for encainide evoked by a synthetic antigen and an immunologically homologous tracer (Class 424/12). Encainide is an antiarrhythmic drug of the piperidine series (Class 260/293.51) having the systematic chemical name 4-methoxy-2'-[2-(1-methyl-2-piperidyl)ethyl]benzanilide. The novel hapten for preparation of the antigen, and the novel tracer are of the same structural type. Encainide is the subject of U.S. Pat. No. 3,931,195 patented January 6, 1976 and has the following structural formula.

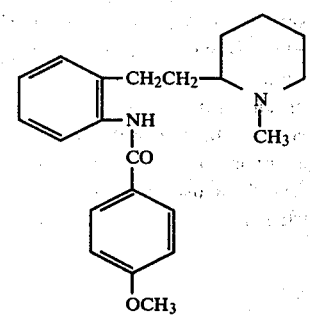

Formula I

DESCRIPTION OF THE PRIOR ART

The antiarrhythmic properties of encainide, also referred to as MJ 9067, in acute animal models have been described by Byrne, et al., Journal of Pharmacology and Experimental Therapeutics, 200, 147–154 (1977). No method for the determination of the concentration of the drug in biological fluids such as blood plasma or blood serum following dosage with the drug has been previously reported.

SUMMARY OF THE INVENTION

An immunoassay method for encainide in blood plasma or urine following oral or intravenous doses of the drug to human subjects has been invented. Antibodies to encainide are prepared by immunizing rabbits with an immunologically homologous analog of encainide conjugated to bovine serum albumin. A further immunologically homologous analog of encainide having an $I^{125}$-labeled tyramine moiety in its structure is used as a tracer. The assay has a maximum sensitivity of 0.3 ng of encainide per milliliter of plasma or urine.

DETAILED DESCRIPTION OF THE INVENTION

The antigenic material useful in the formation of the antibody required for the present assay has the following structural formula.

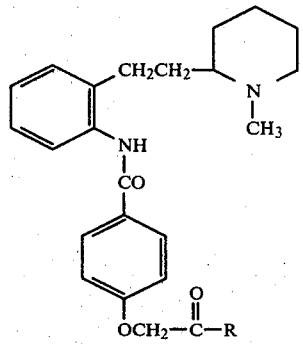

Formula II

In the foregoing structural formula, R represents an immunogenic carrier material. Immunogenic carrier materials include those materials which have the property of eliciting an immunogenic response in a host animal and which can be covalently coupled by an acylation process with the acid shown in Formula III or an equivalent acylation reactive form thereof. The hapten in the antigen of Formula II is the acyl group of the carboxylic acid, [4-[[[2-[2-(1-methyl-2-piperidinyl)ethyl]phenyl]amino]carbonyl]phenoxy]acetic acid, which is shown in Formula III

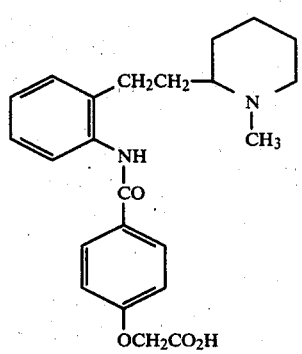

Formula III

Suitable immunogenic carrier materials include proteins, natural or synthetic polypeptides, such as polylysine, or copolymers of amino acids, polysaccharides, and the like. Proteins are particularly preferred as immunogenic carrier materials and most preferred is bovine serum albumin. The protein, of course, must be foreign to the animal host in which the antibody for use in the present assay is to be evoked. For the present assay, the rabbit is employed, but other animals including horse, goat, guinea pig, rat, cow, sheep, etc., can be adapted for the purpose.

The covalent coupling of the hapten to the immunogenic carrier material can be carried out in any of a variety of fashions which have been established in the art. The hapten can be converted to an isolatable active form for coupling purposes such as an acyl halide, ester, or anhydride, or methods which do not involve isolation of an active intermediate may be employed. The particular active form chosen, whether isolated or not, will depend upon the nature of the immunogenic carrier material to which the hapten is to be coupled. Methods commonly available for the formation of esters are suitable when a polysaccharide is employed as the immunogenic carrier material while methods suitable for the formation of amides or peptides are employed when a protein is immunogenic carrier material.

Proteinaceous carrier materials are preferred for practical reasons according to the present invention, as are coupling methods which do not involve isolation of an active intermediate. A number of good methods are available. A particularly suitable group of coupling agents comprise the carbodiimides, most preferably dicyclohexylcarbodiimide or 1-ethyl-3-(3-dimethylaminopropyl)carbodiimide either as the free base or as the mineral acid addition salt such as the hydrochloride salt. Conventional conditions for the coupling reaction are operative. The carbodiimides generally utilize a slightly acidic reaction medium, for instance, a medium in the range of pH 3 to 6.5 but preferably from about pH 4 to 6.5. Another method is via a mixed anhydride intermediate such as that formed by reaction of the acid of Formula III with isobutyl chloroformate in the presence of a strong base tertiary amine. Isolatable active forms include the p-nitrobenzyl ester, and the N-hydroxysuccinimide ester.

EXAMPLE 1

Procedure for the Preparation of [4-[[[2-[2-(1-Methyl-2-piperidinyl)ethyl]phenyl]amino]-carbonyl]phenoxy]acetic Acid (Formula III)

A solution of 338 mg. (1 millimole) of 4-hydroxy-2'-[2-(1-methyl-2-piperidyl)ethyl]benzanilide source, U.S. Pat. No. 3,931,195, column 33, line 65), in 2 ml. of dimethylformamide is added dropwise with stirring to a solution of 53 mg. (2 millimoles) of sodium hydride in approximately 5 ml. of dimethylformamide. The temperature is maintained at 45° C. by immersion of the reaction vessel in an oil bath during the reaction period. Ethyl chloroacetate, 5 millimoles, is then added dropwise which results in the immediate precipitation of sodium chloride with the addition of each drop. When the addition is complete, the insoluble material is removed by filtration, and the filtrate is dried by evaporation. The residue is heated to 60° C. with 5 ml. of 1 N sodium hydroxide for 4 hrs. in order to hydrolyze the ester. The mixture is then clarified by centrifugation and the clear supernatant liquid neutralized with concentrated hydrochloric acid, basified with 0.5 M. sodium carbonate, and extracted with ether. The extraction from sodium carbonate is for the purpose of removing any unreacted phenolic starting material. The aqueous phase is again acidified with concentrated hydrochloric acid to approximately pH 3 and then dried by concentration on a rotary evaporator. The residue is suspended in warm acetone, and ethanol is added to dissolve the product. Insoluble material is removed by filtration, and the filtrate is mixed with ethyl ether to precipitate the product which is collected on a filter and washed with hot ether, and dried. The product is a tan powder exhibiting a single spot on thin-layer chromatography at $R_f$ 0.3 using acetone:methanol:acetic acid 5:5:1 and visualized with iodoplatinate reagent, UV absorption $\lambda_{max}=258$ nm, $\epsilon_{max.}=1.4\times 10^4$ in aq. 0.5 M $Na_2CO_3$.

EXAMPLE 2

Procedure for the Preparation of the Antigen of Formula II

A portion of the acid prepared in Example 1, 10 mg., is dissolved in 5 ml. of water and basified to pH 4.7–5.0. 1-Ethyl-3-(3-dimethylaminopropyl)carbodiimide, 25 mg., is added while maintaining the acidity of the reaction mixture in the foregoing pH range by the addition of 0.1 N hydrochloric acid. From 1.5 to 2 hrs. with stirring are required for this stage of the reaction. The solution is then adjusted to pH 7–8 with 1 N sodium hydroxide and 3.9 mg. of bovine serum albumin (dry basis) is added. The reaction mixture is allowed to stir overnight at room temperature. The solution is then dialyzed against 0.05 M sodium carbonate for several days and the concentration of the antigen in the solution is estimated by UV absorption.

EXAMPLE 3

Immunization of Rabbits with Antigen of Formula II

An aliquot of the dialyzed solution produced in Example 2 is diluted with isotonic saline solution so that 1.2 ml. thereof contains about 200 mcg. of bovine serum albumin. Freund's complete adjuvant, 1 ml., is added and the mixture is mixed vigorously until a thick creamy emulsion is obtained. New Zealand white rabbits are then injected intradermally with this material at multiple sites using 2 ml. of the emulsion for each rabbit. The rabbits are bled from the ear vein at periodic intervals and the blood assayed for antibodies. All rabbits show detectable antibodies six weeks after the immunization. For use in the assay, a blood sample is taken from an immunized animal, and the serum separated. The rabbit antiserum is then diluted and used as indicated below in the assay procedure.

A labeled tracer preferred for use in the assay has the following structural formula.

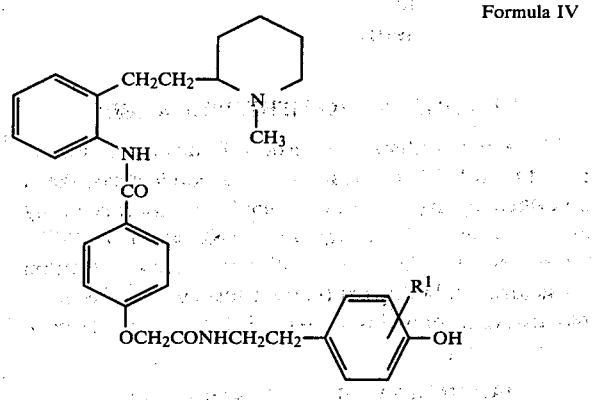

Formula IV

In Formula IV, $R^1$ refers to one or more ring attached $I^{125}$ atoms. $I^{125}$ is a gamma ray emitting isotope of iodine with a half life of 60 days suiting it for laboratory assay use. It is convenient for the preparation of immunoassay tracer materials because of the chemical reactivity of iodine. Other types of labeling elements may be employed such as those which are detectable by fluorescence, electron spin resonance, or enzymatic activity.

The compound of Formula IV is prepared by the N-acylation of tyramine, 2-(4-hydroxyphenyl)ethylamine, with the acid of Formula III or an acylation-activated derivative thereof such as the anhydride, a mixed anhydride, acid halide, or reactive ester thereof in much the same manner as in preparing the antigen of Formula II. The resulting amide of Formula V is then iodinated by reaction with a source of the molecular iodine isotope.

Formula V

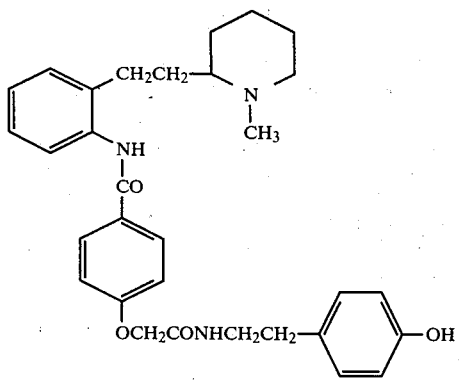

Iodination can be readily carried out by using sodium iodide containing isotope 125 iodine in an oxidative medium which releases $I^{125}$ from the sodium iodide for reaction with the reactive phenolic ring of the compound of Formula V. The following procedure is illustrative in which N-chloro-4-methylbenzenesulfonamide sodium salt (Chloramine-T) is used as oxidizing agent. It is not necessary to fully characterize the iodinated product, but it is believed that $R^1$ in the above formula is predominantly a single ring-attached $I^{125}$ atom in the ortho position to the OH group which is the preferred form. The incorporation of an additional $I^{125}$ atom is possible and this is in no way deleterious. Those substances of Formula IV wherein $R^1$ is from 1 to 2 ring attached $I^{125}$ atoms are included within the present invention.

EXAMPLE 4

Preparation of N-[2-(4-Hydroxyphenyl)ethyl]-2-[4-[[[2-[2-(1-methyl-2-piperidinyl)ethyl]phenyl]amino]carbonyl]phenoxy]acetamide (Formula V)

The product of Example 1, 5.5 mg. (0.014 millimoles) is dissolved in about 2.5 ml. of dimethylformamide and 1.4 ml. of 1 N sodium hydroxide (0.014 millimoles) and 0.2 ml. of triethylamine (0.014 millimoles) are added. The reaction flask is cooled in an ice bath and 0.2 ml. (0.015 millimoles) of isobutyl chloroformate is added. The mixture is stirred gently for 20 min. to allow formation of the mixed anhydride. A solution of 2.4 mg. (0.014 millimoles) of tyramine hydrochloride in dimethylformamide is prepared, neutralized with 1.4 ml. of 1 N sodium hydroxide, and added to the reaction mixture. The reaction mixture is allowed to warm to room temperature with stirring for 60 min. The progress of the amidification reaction is measured by thin-layer chromatography using the solvent system chloroform:methanol:acetic acid (40:10:0.5) in which the starting materials remain near the origin and the product of Formula V migrates with $R_f$ 0.6. After completion of the reaction, the mixture is dried on a rotary evaporator and the residue is resuspended in a small amount of dimethylformamide. Water is added, and the mixture is neutralized with 0.5 M sodium carbonate and the product extracted into ether. The ether phase is dried, the residue dissolved in methanol, and the product purified by thin-layer chromatography using the above solvent system. The major band which appears at $R_f$ 0.6 is eluted from the silica gel with ethanol, concentrated and rechromatographed. The resulting material is used without further purification or characterization for iodination as described below.

EXAMPLE 5

Preparation of Iodinated Tracer of Formula IV

The product of Example 4, 0.3 mcg., is dissolved in 5 μl. of 0.01 M phosphate buffer (pH 7.6) and treated with $NaI^{125}$, 2 mCi, in 25 μl. of 0.5 M phosphate buffer. A solution containing 25 mcg. of N-chloro-4-methyl-benzenesulfonamide sodium salt in 10 μl. of 0.01 M phosphate buffer is then added. The reaction vial is carefully mixed for 1 min. after which 10 μl. of a solution containing 62.5 mcg. of sodium metabisulfite in 0.01 M phosphate buffer is added. The radiolabeled product is separated by thin-layer chromatography on silica gel using chloroform:methanol:acetic acid (40:10:0.5) as development solvent. The location of the radioactive spot is located by exposing a medical x-ray film to the plate and scraping the radioactive spot corresponding to the iodinated product from the plate. The iodinated product migrates slightly faster than the unreacted tyramide starting material which can be detected on the plate by UV fluorescence. Care is exercised in excising the radioactive zone so that unreacted material is left on the plate. The radiolabeled tracer is then eluted from the silica gel with 1 ml. of ethanol and diluted as described below for use in the assay.

EXAMPLE 6

Assay Procedure

Plasma samples from individuals to whom encainide has been administered having a measured volume in the range of from 0.2 to 1.0 ml. are diluted to 1 ml. with water and mixed with 1 ml. of 0.2 N sodium hydroxide and 10 ml. of ether. The sample tubes are capped and mixed vigorously for extraction. The tubes are then centrifuged and 9 ml. of the ether phase is removed by aspiration and transferred to a clean tube. The ether phase is evaporated under nitrogen and the residue is suspended in 1 ml. of PBG buffer solution. PBG buffer solution consists of 0.15 M sodium phosphate (pH 7.6) containing 0.1% gelatin and 0.1% sodium azide. A higher dilution of extract residue may be used if convenient. An aliquot of this suspension having a volume of 0.1 ml. is added to 0.4 ml. of PBG buffer, followed in sequence by 0.1 ml. of the tracer solution produced in Example 5 previously diluted with PBG buffer to emit 15,000–20,000 counts per minute per 0.1 ml. aliquot measured in a Nuclear Chicago gamma counter or other suitable counter, and 0.2 ml. of diluted rabbit antiserum produced as described in Example 3. Dilution of the antiserum is made with a solution containing 2% normal rabbit serum in PBG buffer containing in addition 0.05 M ethylenediaminetetraacetic acid disodium salt so that sufficient antiserum is present in the 0.2 ml. volume to combine with approximately one-half the amount of tracer employed. Control tubes are prepared as above containing either no test sample or test solutions of known amounts of encainide ranging from 10,000 pg/tube to 2 pg/tube. The tubes are mixed and allowed to stand at room temperature for 4 hrs. Sufficient goat antirabbit gamma globulin serum is then added to precipitate all of the rabbit serum gamma globulins and the precipitate is collected by centrifugation. The solid material remaining after aspiration of the supernatant liquid contains the precipitated antibody containing amounts of encainide from the test sample and the labeled tracer in proportion to their concentrations in the test mixture. The precipitated antibody is counted in a gamma counter and the amount of encainide in the original sample is determined by interpolation from a control curve prepared by plotting the counts per minute versus amount of encainide in the reference standard samples.

The foregoing procedure is based upon the principle that the rabbit antiserum will combine with the labeled tracer in specific reproducible amount when a fixed amount of the labeled tracer and a fixed amount of the rabbit antiserum are used in replicate tests. A fixed amount of labeled tracer is employed. The gamma globulin protein fraction containing the tracer antiserum complex is isolated and the amount of tracer contained therein determined by virtue of the label, in this instance, the number of gamma emissions per minute. Such a system in the presence of a sample containing encainide, which is bound as an antibody complex by the same antiserum, will result in the formation of an tracer antiserum complex containing less of the tracer than the control specimen as above due to the competitive binding of a portion of the antiserum by the encainide. Thus, by preparing a graph relating on one axis the counts per minute of the isolated tracer antibody complex to the amount of encainide in each of a series of test samples, it is possible to determine by interpolation the amount of encainide in an unknown sample by measuring the counts per minute of the collected tracer antiserum complex. Conversely, since a fixed excess of tracer is employed, the tracer measurement may be made on the supernatent liquid from which the antibody complex has been isolated since the amount remaining in the supernatent is the difference between the known amount originally employed, and the amount precipitated in the antibody complex. The foregoing is in accord with usual practice for immunoassays of the present type.

The specificity of the assay was determined by the preparation of control graphs as described above but employing several samples having different known amounts of the following substances, which are presumed metabolites of encainide, instead of encainide as reference standard.

A. 4-Hydroxy-2'-[2-(1-methyl-2-piperidyl)ethyl]benzanilide
B. 4-Methoxy-2'-[2-(2-piperidyl)ethyl]benzanilide
C. 4-Hydroxy-2'-[2-(2-piperidyl)ethyl]benzanilide The graph for each of these substances was linear and parallel with that for encainide, but displaced therefrom indicating fewer counts for these substances for samples of the same weight. The following numerical values for the relative binding activities were determined from this set of graphs, assigning encainide an arbitrary value of 100: Compound A, 18; Compound B, 8; Compound C, 0.8. These figures mean that for a sample containing 100 pg. of Compound A, the assay would reflect 18 pg. of encainide, for Compound B, 8 pg., and for Compound C, 0.8 pg. The extraction procedure used to treat the plasma samples is such that none of Compound A or Compound C (these are phenolic compounds) is extracted into the test medium from the plasma sample. Only Compound B, if present in the plasma sample, is extracted with the encainide into the test medium. Its relative binding activity (8 vs. 100 for encainide) is so low that its presence can be neglected as not significantly affecting the results.

It has been found that the assay procedure of Procedure 6 can be modified to omit the ether extraction of the plasma sample without materially affecting the assay results. Apparently presumed metabolites A. and C. identified above or other cross-reacting substances are absent or present in such small amounts as to not affect the assay results. According to this mode of operation, 0.1 ml. of the plasma sample, diluted if necessary with PBG buffer according to the concentration of encainide contained therein, is substituted directly for the aliquot of the PBG buffer suspension referred to in the seventh sentence of the procedure.

I claim:
1. A method for the assay of encainide in a test sample which comprises:
   (a) preparing a mixture of said sample with a measured amount of labeled tracer which is immunologically homologous with encainide,
   (b) reacting therewith antiserum containing an antibody having the property of competitively binding as antigen encainide and said tracer to form an antigen antibody complex wherein such amounts of said antiserum and said tracer are employed that only a portion of said tracer is combined as said antigen antibody complex,
   (c) thereafter separating said mixture into an antigen antibody complex-containing portion and a supernatent liquid-containing portion,
   (d) measuring the amount of tracer in at least one of said complex-containing portion and said supernatant liquid-containing portion, and
   (e) determining the amount of encainide in said sample by comparing said measurement to a group of standard reference measurements made on standard reference samples containing known and differing amounts of encainide and treated identically according to steps (a), (b), (c), and (d) as said test sample.

2. An antigen containing a hapten for the formation of the antibody of claim 1, having the formula

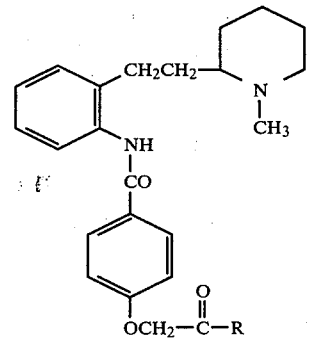

wherein R is a covalently bound immunogenic carrier material, and the balance of the formula is said hapten.

3. The antigen of claim 2 wherein said immunogenic carrier material is a protein.

4. The antigen of claim 2 wherein said immunogenic carrier material is bovine serum albumin.

5. [4-[[[2-[2-(1-Methyl-2-piperidinyl)ethyl]phenyl]amino]carbonyl]phenoxy]acetic acid.

6. The method of claim 1 wherein said tracer contains a radioactive element.

7. A tracer suited for use in the process of claim 6 having the formula

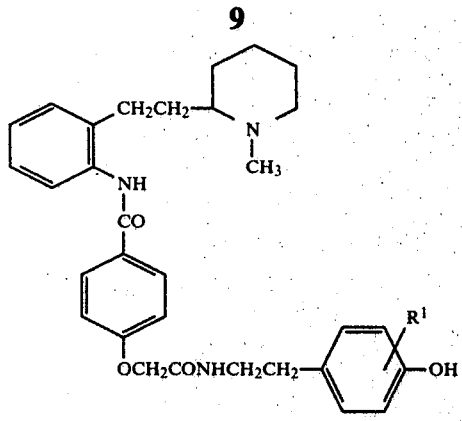
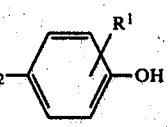
wherein R¹ is from 1 to 2 ring attached $I^{125}$ atoms.
8. The tracer of claim 7 wherein R¹ is a single ring attached $I^{125}$ atom in the ortho-position to the —OH.
9. N-[2-(4-Hydroxyphenyl)ethyl]-2-[4-[[[2-[2-(1-methyl-2-piperidinyl)ethyl]phenyl]amino]carbonyl]-phenoxy]acetamide.
* * * * *